United States Patent
Connelly et al.

(10) Patent No.: US 9,937,290 B2
(45) Date of Patent: *Apr. 10, 2018

(54) CONSTANT RATE FLUID DELIVERY DEVICE WITH SELECTABLE FLOW RATE AND TITRATABLE BOLUS BUTTON

(71) Applicant: Becton, Dickinson and Company, Franklin Lakes, NJ (US)

(72) Inventors: Robert I. Connelly, Raleigh, NC (US); Kenneth G. Powell, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 851 days.

This patent is subject to a terminal disclaimer.

(21) Appl. No.: 14/324,839

(22) Filed: Jul. 7, 2014

(65) Prior Publication Data

US 2015/0011937 A1   Jan. 8, 2015

Related U.S. Application Data

(63) Continuation of application No. 10/777,078, filed on Feb. 13, 2004, now Pat. No. 8,771,227, which is a
(Continued)

(51) Int. Cl.
*A61M 5/168* (2006.01)
*A61M 5/142* (2006.01)
(Continued)

(52) U.S. Cl.
CPC .... *A61M 5/16881* (2013.01); *A61M 5/14248* (2013.01); *A61M 5/148* (2013.01); *A61M 5/14586* (2013.01)

(58) Field of Classification Search
CPC .............. A61M 5/148; A61M 5/14248; A61M 5/16881; A61M 5/14276; A61M 5/14586
See application file for complete search history.

(56) References Cited

U.S. PATENT DOCUMENTS 2,509,456 A   5/1950   Saballus
4,258,711 A   3/1981   Tucker et al.
(Continued)

FOREIGN PATENT DOCUMENTS

DE         854318 C    11/1952

*Primary Examiner* — Matthew F Desanto
(74) *Attorney, Agent, or Firm* — Dickinson Wright, PLLC

(57) ABSTRACT

A wearable, self-contained drug infusion device is disclosed that is capable of achieving the precise flow rate control needed for dose-critical drugs such as insulin. In preferred embodiments of the device, at least two flow channels are utilized in conjunction with a series of valves for providing a user with selectable, constant flow rate control. The device can be made with small dimensions so that it can be worn by the user with a minimum of discomfort and inconvenience. In addition, the simple mechanical nature of the device provides the user with close control over the flow rate, which is required for safe and effective delivery of insulin and other drugs. Also, the absence of electronic components allows the device to be manufactured inexpensively. The device is provided with a first channel that is long and narrow, functioning as a flow restrictor. The first channel is preferably provided in a serpentine pattern. A second channel is also provided that has a larger cross section so that flow is not restricted. A series of valves are used to force the flow of fluid through a selectable portion of the serpentine portion of the first channel before entering the remainder of the second channel and flowing to the delivery cannula. In one embodiment of the device, a needle port is provided in fluid communication with the delivery cannula for delivering bolus injections. In another embodiment, a bolus button is provided for delivering bolus injections. A flow restrictor is preferably included in the bolus button to limit the rate at which the bolus button refills.

12 Claims, 9 Drawing Sheets

Related U.S. Application Data continuation of application No. 09/931,102, filed on Aug. 17, 2001, now Pat. No. 67,002,779.

(60) Provisional application No. 60/226,017, filed on Aug. 18, 2000.

(51) Int. Cl.
*A61M 5/145* (2006.01)
*A61M 5/148* (2006.01)

(56) References Cited

U.S. PATENT DOCUMENTS

| | | | |
|---|---|---|---|
| 4,548,607 A * | 10/1985 | Harris | A61M 5/1428 604/153 |
| 4,715,852 A | 12/1987 | Reinicke et al. | |
| 4,838,887 A | 6/1989 | Idriss | |
| 4,874,386 A * | 10/1989 | O'Boyle | A61M 5/16881 604/135 |
| 4,886,499 A | 12/1989 | Cirelli et al. | |
| 5,009,251 A * | 4/1991 | Pike | A61M 5/16881 137/561 A |
| 5,370,635 A | 12/1994 | Strausak et al. | |
| 5,445,616 A | 8/1995 | Kratoska et al. | |
| 5,575,770 A | 11/1996 | Melsky et al. | |
| 5,667,504 A | 9/1997 | Baumann et al. | |
| 5,848,990 A | 12/1998 | Cirelli et al. | |
| 5,908,414 A | 6/1999 | Otto et al. | |
| 6,074,369 A | 6/2000 | Sage et al. | |
| 6,485,461 B1 | 11/2002 | Mason et al. | |
| 6,537,268 B1 | 3/2003 | Gibson et al. | |
| 6,554,822 B1 * | 4/2003 | Holschneider | A61M 5/14276 604/156 |
| 6,562,000 B2 | 5/2003 | Thompson et al. | |
| 6,635,049 B1 | 10/2003 | Robinson et al. | |
| 6,702,779 B2 * | 3/2004 | Connelly | A61M 5/14248 604/890.1 |
| 8,771,227 B2 * | 7/2014 | Connelly | A61M 5/14248 604/131 |

\* cited by examiner

CONSTANT RATE FLUID DELIVERY DEVICE WITH SELECTABLE FLOW RATE AND TITRATABLE BOLUS BUTTON

This application is a continuation of Ser. No. 10/777,078, filed Feb. 13, 2004, which is a continuation of Ser. No. 09/931,102, filed Aug. 17, 2001, now U.S. Pat. No. 6,702,779, which claims the benefit under 35 U.S.C. § 119(e) of U.S. Provisional Application Ser. No. 60/226,017, filed Aug. 18, 2000.

FIELD OF THE INVENTION

The present invention relates generally to fluid delivery devices. In particular, it is concerned with a self-contained fluid delivery device that can be used to deliver a variety of medications at a selectable flow rate, and which may include a bolus port for intermittent immediate controlled delivery of additional doses of fluid.

BACKGROUND OF THE INVENTION

Diabetes is a chronic disease that is caused by both hereditary and environmental factors. It is characterized by the body's inability to control glucose levels. Left untreated, it causes damage to the circulatory and nervous systems and results in organ failures, amputations, neuropathy, blindness and eventually death. It has been definitively shown that the cost of the complications related to diabetes significantly exceeds the cost of therapy. The Diabetes Control and Complications Trial (DCCT) was a ten-year study of 1400 patients to assess the benefits of close control of blood glucose levels. The study found that such close control provided 50% to 75% reductions in retinopathy, nephropathy, neuropathy and cardiovascular risk.

There are roughly 17.5 million people with diabetes in the United States and Europe, and about 60 million more worldwide. Roughly 35% of these people use insulin to maintain close control of their glucose levels. Proper control of blood glucose levels through programmed insulin injection or infusion allows a high quality of life and a life expectancy of an additional 35 to 40 years from diagnosis.

Currently, there are two principal modes of daily insulin therapy. The first mode includes syringes and insulin pens. These devices are simple to use and are relatively low in cost, but they require a needle stick at each injection, typically three to four times per day. The second is infusion pump therapy, which entails the purchase of an expensive pump that lasts for about three years. The initial cost of the pump is a high barrier to this type of therapy. From a user perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

The typical patient on intensive therapy injects insulin to provide a basal level and then takes supplemental boluses prior to meals during the day. Those on infusion pumps program their pumps to mimic this type of delivery schedule. There are several existing or anticipated means of insulin therapy that a patient might consider.

The first are so-called oral agents that enhance the ability of the body to utilize insulin. Typical compounds include sulfonylureas, biguanides and thiazolidinediones. Oral agents are initially appropriate for Type 2 diabetics, whose bodies produce some insulin, although after a period of years these patients generally need to supplement with additional insulin. For Type 1 diabetics, the body does not produce insulin and these agents are not effective.

Once the oral agents are no longer effective, insulin is injected using syringes or multi-dose insulin pens. The syringe is the least expensive means of delivery, but many patients are willing to pay a premium for the convenience of the insulin pen.

A recent advance has been the development of extremely long-acting insulins. While regular insulins have a physiological onset in 10 minutes and peak activity in about 90 minutes, current long-acting insulins peak in roughly 8 hours. This type of insulin can be taken in the morning and can be accompanied by bolus delivery at meals. The alternative of simply taking all of one's insulin requirement in basal delivery is believed by many to be therapeutically unsound. Insulin resistance is theorized to build as a result of high concentrations of insulin in the bloodstream, and as a result ever increasing amounts of insulin are necessary to control blood glucose levels. Unfortunately, the basal plus bolus profile still results in the same high and undesirable frequency of injections, typically four per day. Long-acting insulin does provide good therapy for those patients whose bodies benefit from supplemental basal insulin, but this is a temporary condition and simply delays a more rigorous insulin injection regimen for six months to two years.

As their interest in intensive therapy increases, users typically look to insulin pumps. However, in addition to their high cost (roughly 8 to 10 times the daily cost of syringe therapy) and limited lifetime, insulin pumps represent relatively old technology and are cumbersome to use. Also, from a lifestyle standpoint, the tubing (known as the "infusion set") that links the pump with the delivery site on the user's abdomen is very inconvenient and the pumps are relatively heavy, making carrying the pump a bother.

A new method of insulin delivery currently undergoing development is pulmonary delivery. The principal issue with pulmonary delivery is criticality of dose, as pulmonary delivery is relatively inefficient and difficult to quantify. As a result, it will be difficult to keep blood glucose levels in control with this delivery form, although it may prove very useful as a supplement for bolus delivery at mealtime. The inefficiency of delivery (currently about 10%) significantly drives up the cost of pulmonary therapy. The implications of chronic inhalation of insulin are also unknown.

In summary, patients on oral agents eventually move to insulin, and existing pump therapy is very expensive. Interest in better therapy is on the rise, accounting for the observed growth in pump therapy and increased number of daily injections. What is needed to fully meet this increased interest is a form of insulin delivery that combines the best features of daily injection therapy (low cost and ease of use) with those of the insulin pump (continuous infusion, precision dosing and variable delivery rates), and that avoids the disadvantages of each. This will allow a greater number of patients to have access to improved insulin therapy at lower cost.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices cannot provide precise control over the flow rate of the drug at a low delivery cost, and are thus not compatible with dose-critical drugs such as insulin. In addition, devices that operate with fixed insulin flow rates may meet cost targets but still require bolus injections at mealtimes. Ultimately, therefore, these existing devices do not represent an optimal alternative to infusion pumps.

SUMMARY OF THE INVENTION

The present invention substantially avoids the disadvantages and limitations of the prior art by providing a wearable, self-contained drug infusion device that is simple in construction but is capable of achieving the precise and variable flow rate control needed for dose-critical drugs such as insulin. The flow rate is selectable by the user to accommodate a wide range of individual metabolic rates. The device is significantly less expensive to manufacture than typical insulin pumps because electronic components are not necessary. Furthermore, the device is dependable because it can incorporate a purely mechanical process.

In a preferred embodiment of the invention, the drug infusion device comprises a housing, a reservoir in the housing for containing a supply of fluid, and a cannula (needle) for delivering the fluid to a patient. The device further comprises first and second flow channels for delivering the fluid from the reservoir to the delivery cannula. The first flow channel is arranged in a serpentine pattern to increase its effective length. The cross section of the first channel (also referred to herein as the "serpentine channel") is smaller than the cross section of the second channel. The second channel is further comprised of a plurality of nodes that are in fluid communication with the serpentine channel. The serpentine channel is divided into a number of sections, and each section is associated with a node in the second channel. The nodes can be selectively turned off to allow or prevent fluid from flowing through the node. Thus, when a node is open, fluid is able to pass through the second channel, which imparts less flow restriction due to its larger cross section and shorter length. By closing one or more nodes, fluid flowing from the reservoir to the needle is forced to travel through the portions of the serpentine channel associated with the closed nodes. Closing more nodes increases the effective length of the serpentine channel that the fluid must flow through. Thus, by closing more nodes, the effective length of the serpentine channel is increased, the flow restriction is increased, and the flow rate is decreased.

In a preferred embodiment of the invention, a disc spring (also referred to as a Belleville spring) is included within the housing. When the device is activated, the Belleville spring engages and pressurizes the fluid reservoir, causing the fluid to flow out of the reservoir and toward the needle. The Belleville spring applies constant pressure on the reservoir, causing the flow rate to remain constant over time despite changes in the fluid volume in the reservoir.

In another preferred embodiment, the first and second channels are formed in the housing, with one wall of the channels being formed by a flexible membrane that is fixedly attached to the housing. The nodes of the second flow channel are defined by indentations in the housing along the second flow channel. A flow rate selection device is movably attached to the housing, such that the flexible membrane is sandwiched between the housing and the flow rate selection device. The flow rate selection device is provided with detents which correspond in shape to the indentations in the housing. The flow rate selection device may be moved into alignment with the indentations so that a selected number of detents aligns with corresponding indentations. Because the shape of the detents matches the indentations, the detents push the flexible membrane into the indentations, preventing the flow of fluid through the nodes. Thus, the detent, membrane and indentation act like a valve at each node.

In another preferred embodiment the device is provided with a bolus port for delivering a bolus injection of medicament. The port comprises an opening in the housing in communication with the proximal end of the delivery cannula. The opening is preferably sealed with an elastomeric septum so that a syringe may be used to deliver an additional dose of medicament through the port to the user immediately. When the bolus injection is completed and the syringe is removed, the septum reseals, preventing medicament from escaping through the bolus port and maintaining the hermetic seal around the device. The bolus port may also include a cone shaped guide for guiding the needle of the syringe to the membrane.

BRIEF DESCRIPTION OF THE DRAWINGS

The various objects, advantages and novel features of the present invention will be more readily understood from the following detailed description when read in conjunction with the appended drawings, in which.

Throughout the drawings, like reference numerals will be understood to refer to like parts and components.

DETAILED DESCRIPTION OF THE PREFERRED EMBODIMENTS

Figure 1:
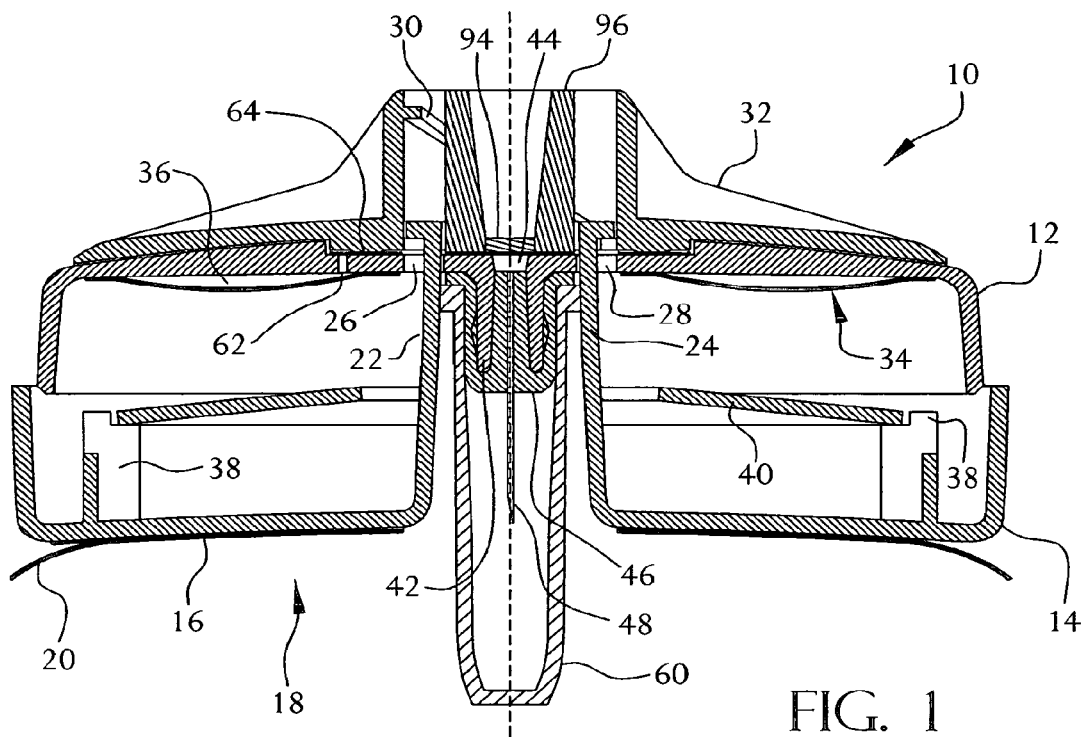
FIG. 1 is a cross-sectional view of a first embodiment of a fully assembled drug infusion device in the pre-use configuration.

A fluid delivery device constructed in accordance with a first embodiment of the present invention is shown in FIGS.

1-5. The device 10 may be used for the delivery of a liquid medication, preferably but not necessarily insulin, by continuous infusion into or through the skin of a patient. The device 10 is intended to be worn on the surface of the skin by the user, with a cannula (hollow needle) penetrating into the user's skin or transcutaneously through the skin into the subcutaneous tissue. The device 10 does not require any electronic components, and is intended to be simple and inexpensive to manufacture while providing a selectable constant flow rate of medicament to the patient. Although the present invention is not limited to specific dimensions, the device 10 preferably has an overall size (excluding the delivery cannula and the cannula shield 100) of about 50 millimeters in diameter and 12 millimeters in height. The delivery cannula may be rigid or flexible and may have any desired length, but a typical length is between 5 millimeters and 12 millimeters. The cannula shield 60 may be about 15 millimeters in height, making the total height of the device 15 about 27 millimeters. In lieu of a single delivery cannula, a plurality of microneedles may be used to deliver the liquid medication to the skin of the user. Since a typical microneedle length is only 0.5 millimeter, a device 10 constructed using microneedles may have a height dimension not much greater than 12 millimeters. The term "delivery cannula" as used herein will be understood to include not only a hollow needle of the type shown in the drawings, but also one or more microneedles or other structures that deliver liquid medications into or through the skin, whether by skin penetration or otherwise.

FIGS. 1-5 show the assembly of a first embodiment of the device 10. The housing of the device 10 is comprised of a top cover 12 and a bottom cover 14. The bottom cover 14 has a flat surface adapted to be attached to the skin of a patient, and has an adhesive layer 16 on the outer surface 18 covered by a release liner 20. The release liner 20 is removed to expose the adhesive layer 16, so that the device 10 may be attached to the skin of the patient. The device 10 is held together by legs 22, 24 that extend upwardly from the bottom cover 14, through openings 26, 28 in the top cover and engage threads 30 in a selector knob 32.

An annular flexible membrane 34 is attached to the inner surface of the top cover 12 to form a fluid reservoir 36. The membrane 34 is sealed to the top cover 12 at the inner and outer diameter of the membrane 34, forming a fillable space 36 between the membrane 34 and the inner surface of the top cover 12. Heat sealing or any other sealing method suitable to create a fluid tight bond between the membrane 34 and the top cover 12 may be used.

Figure 2:
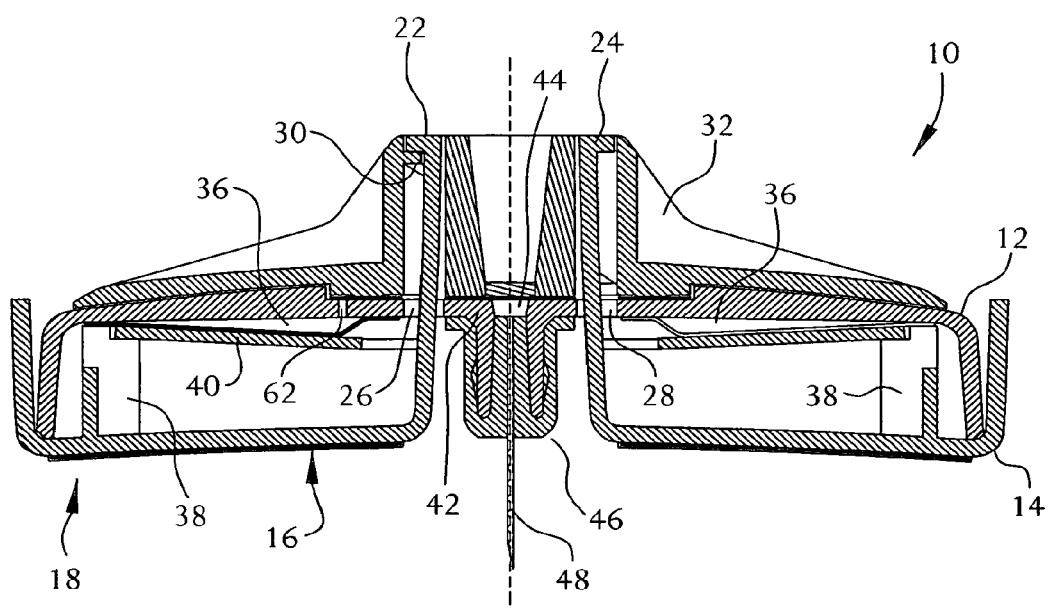
FIG. 2 is a cross-sectional view of a first embodiment of the drug infusion device shown in FIG. 1, in the active use configuration.

The bottom cover 14 has locator bosses 38 adapted to engage a Belleville spring 40. The spring 40 remains unflexed until the device is put into use. Rotating the selector knob 32 causes the threads 30 to force the bottom cover 14 to move closer to the top cover 12, as shown in FIG. 2. When the bottom cover 14 and top cover 12 are forced together, the Belleville spring comes into contact with the membrane 34 and flexes against the membrane 34, causing the fluid within the reservoir 36 to become pressurized. Further details concerning the use of Belleville springs in a fluid reservoir can be found in commonly-assigned U.S. Pat. Nos. 5,957,895 and 6,074,369, both issued to Burton H. Sage and Robert I. Connelly, which are expressly incorporated herein by reference.

The top cover 12 also has a protrusion 42 around a central opening 44 that is adapted to engage a hub 46. The hub 46 retains a cannula 48 and snaps onto the top cover protrusion 42 so that the cannula 48 is in fluid communication with the central opening 44.

Figure 3:
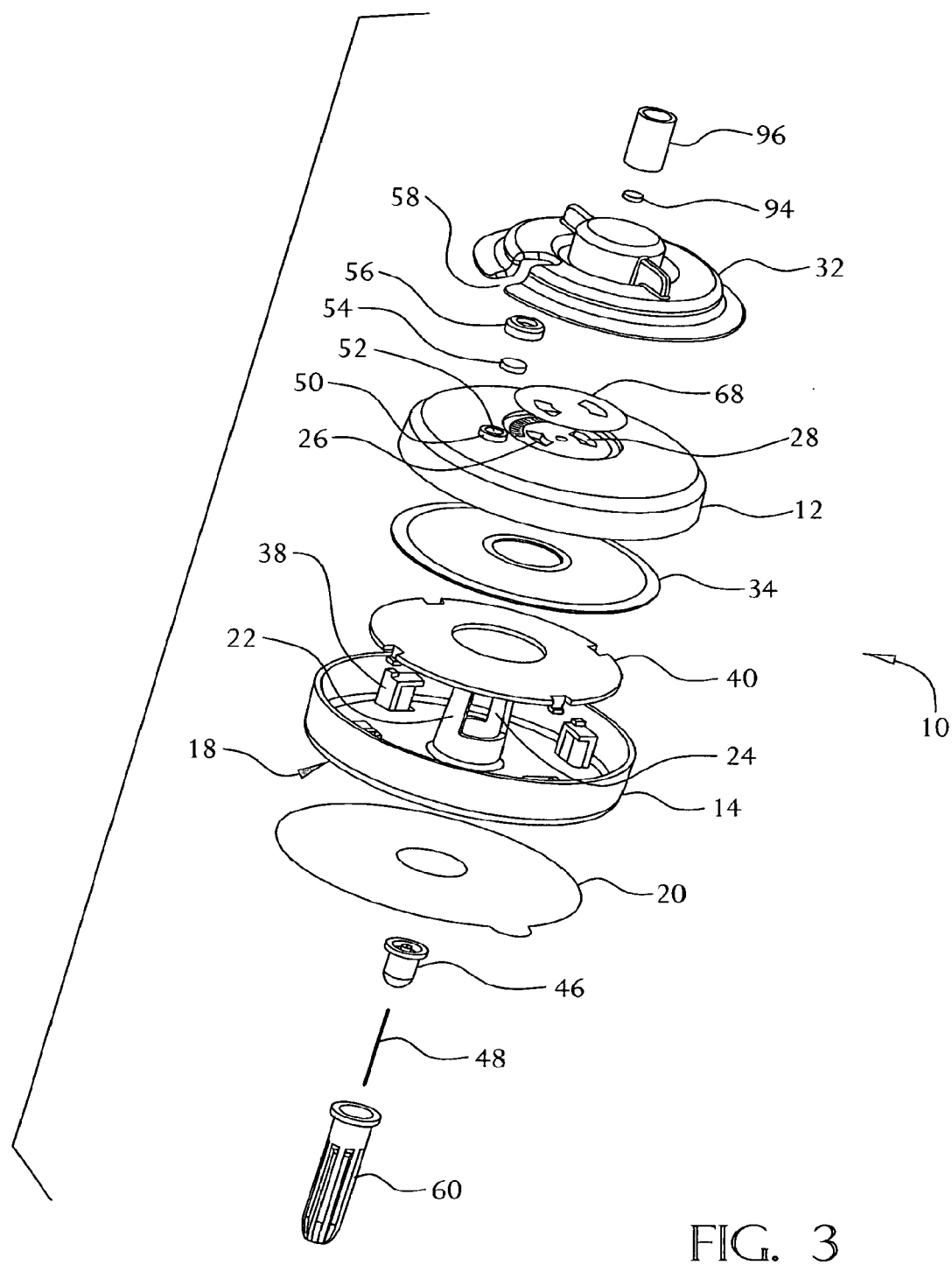
FIG. 3 is an exploded view of the infusion device shown in FIGS. 1 and 2.

Before the device 10 may be used, the reservoir 36 must be filled with medicament. As shown in FIG. 3, a fill port 50 is provided. The port 50 comprises an opening 52 in the top cover 12, a resealable membrane 54 covering the opening, and a cover 56 securing the membrane 54 in place. The resealable membrane 54 allows a syringe to be inserted into the reservoir 36 to fill the reservoir 36 with medicament, while sealing the fill port 50 when the syringe is removed, so that the medicament cannot escape through the fill port 50. The selector knob 32 is provided with a slot 58 so that the fill port 50 is initially accessible. However, once the selector knob 32 is rotated, activating the device 10, it cannot be rotated back to its original position. Thus, the fill port 50 may not be accessed after the device 10 has been activated. This feature guarantees that the device 10 may only be used once.

Figure 4:
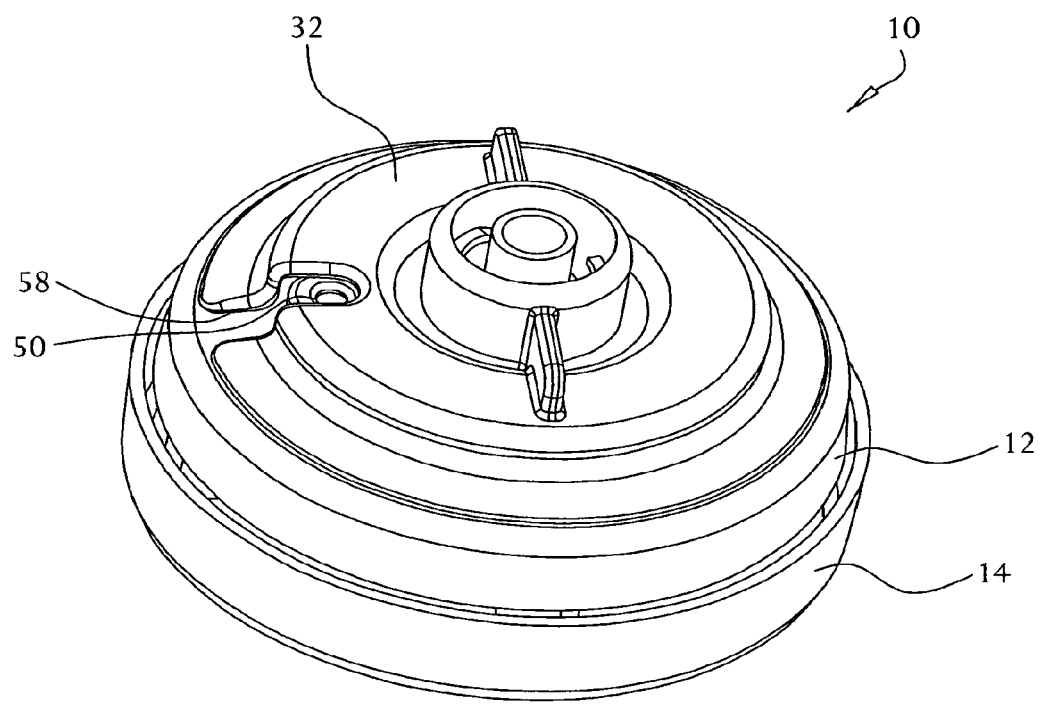
FIG. 4 is a perspective view of the drug infusion device of FIGS. 1 and 2 shown in the pre-use configuration.

In the device's initial configuration, the top cover 12 is separated from the bottom cover 14 as shown in FIGS. 1 and 4. In this position the spring 40 is not pressed against the membrane 34, the cannula 48 is retracted so that it does not extend beyond the lower surface 18 of the bottom cover 14, and the bottom end of the threads 30 engage the legs 22, 24 of the bottom cover 14. A removable cover 60 is placed over the cannula 48 and hub 46 to protect and avoid unintentional contact with the cannula 48.

Figure 5:
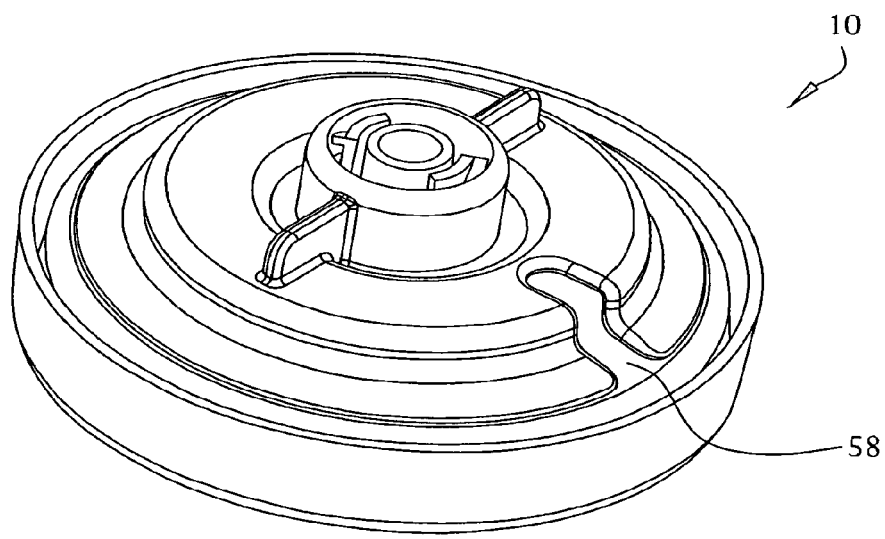
FIG. 5 is a perspective view of the drug infusion device of FIGS. 1 and 2 shown in the active use configuration.

To use the device, the reservoir 36 is filled and the removable cover 60 is removed to expose the cannula 48. Next, the release liner 20 is removed to expose the adhesive layer 16, and the device 10 is attached to the patient's skin. Finally, the selector knob 32 is rotated. As the knob 32 is rotated through the first 180 degrees, the threads 30 force the legs 22, 24 further into the openings 26, 28. As the legs 22, 24 are drawn into the openings 26, 28 the top cover 12 collapses down into the bottom cover 14, as shown in FIGS. 2 and 5. Because the cannula 48 is fixedly attached to the top cover 12, as the device 10 collapses the cannula 44 extends past the lower surface 18 of the bottom cover 14 and into the patient's skin. Next, the spring 40 comes into contact with the membrane 34 and flexes, imparting a precise pressure on the liquid medicament within the reservoir 36. Finally, the selector knob 32 is rotated beyond 180 degrees to select the desired flow rate. The functionality of the selector knob 32 and the flow channels used to select the flow rate will be discussed in greater detail below.

The only path by which liquid medicament may exit the reservoir 36 is through a port 62 formed into the top cover 12. The port 62 allows liquid from the membrane reservoir 36 to flow to the top surface 64 of the top cover 12. The port 62 is in fluid communication with flow channels 66 formed into the top surface 64 of the top cover 12 that lead eventually to the central opening 44 of the top cover 12 and the delivery cannula 48.

Figure 6:
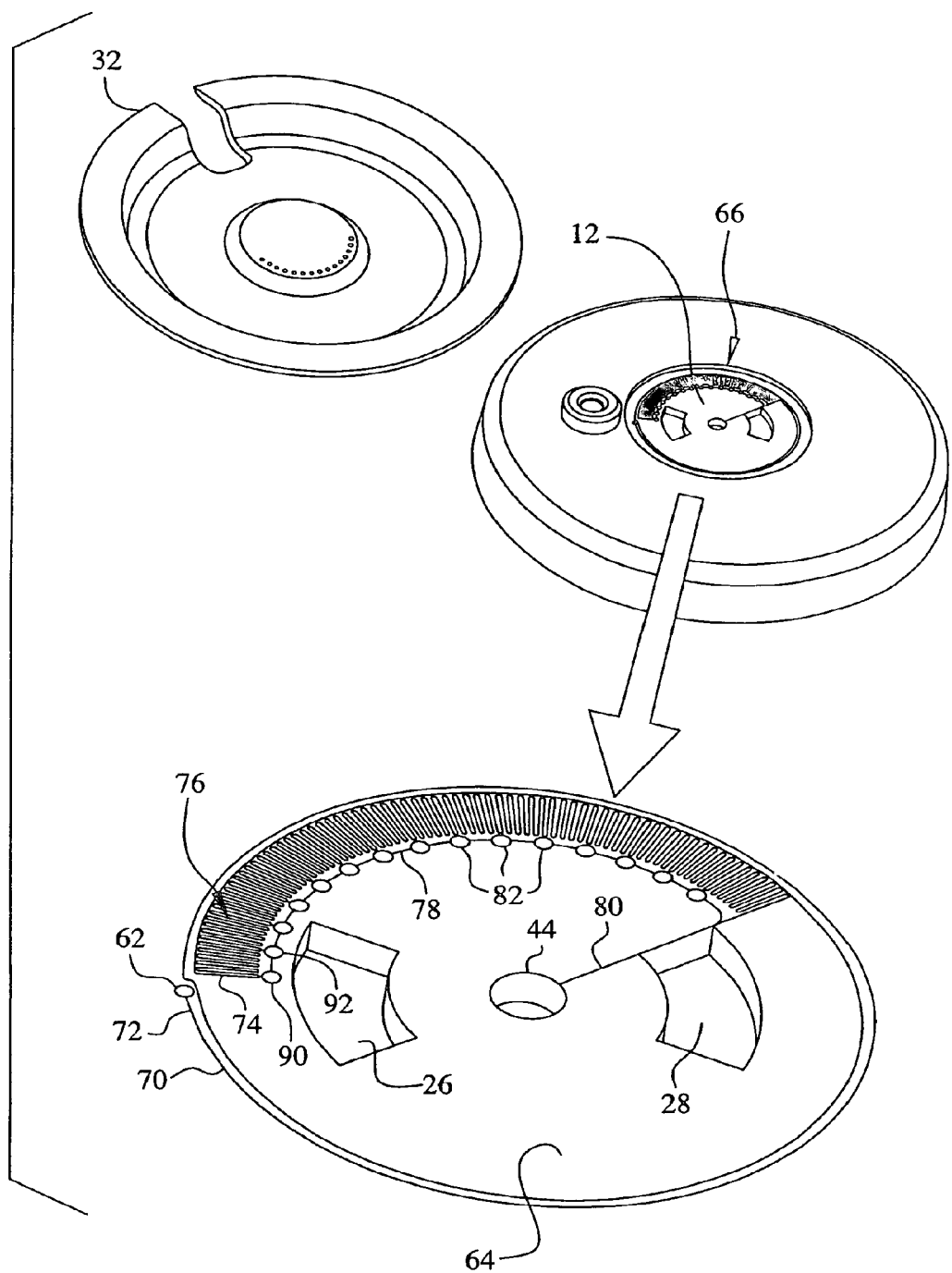
FIG. 6 is a detailed perspective view of flow channels and nodes used to regulate the flow rate in accordance with the present invention.

FIG. 6 shows a detailed view of the flow channels 66 formed into the surface 64 of the top cover 12. The channels 66 have a very small cross section, the smallest being roughly 20 microns wide by 60 microns deep. One possible method of accurately producing channels of this size is the use of photolithography techniques to produce a metal negative of the channels and injection molding of plastic to form the top cover 12 with channels 66 formed into the surface 64. However, the invention is not limited to any particular manufacturing technique, and those skilled in the art will recognize a variety of potential manufacturing methods. The flow channels 66 formed into the surface of the top cover 12 have an open side that is sealed with a flexible membrane 68 that forms one wall of the channels. The membrane 68 is preferably heat sealed to the top cover 12, although it will be recognized that any suitable bonding method could be used. Because the channels 66 are very long with a small cross section, they act as a flow restrictor. The amount of pressure applied by the spring 36 together with the flow restriction caused by the flow channels 66 allows a precisely metered flow of medicament to the patient.

Referring to the detailed view shown in FIG. 6, an initial flow channel 70 has a proximal end 72 and a distal end 74. The proximal end 72 is in fluid communication with the reservoir port 62, and the distal end 74 is in communication with two possible paths. The first path is a primary restrictor channel 76 and the second is a selector channel 78. Both the primary restrictor channel 76 and the selector channel 78 have a proximal end that is in communication with the initial channel 70 and a distal end that is in communication with an exit channel 80. While the primary restrictor 76 and selector 78 channels run generally parallel to each other, the primary restrictor channel 76, due to its preferably serpentine pattern, is much longer than the selector channel 78. The exit channel 80 leads to and is in fluid communication with the central opening 44 and also with the interior of the cannula 48. The primary restrictor channel 76 is preferably formed into a series of closely packed 180 degree turns, making its effective length very long. Furthermore, the primary restrictor channel 76 is roughly 20 microns wide and 60 microns deep. Due to its long length and small cross section, the primary restrictor channel 76 acts as a flow restrictor.

The selector channel 78 runs along the primary restrictor channel 76 in a relatively straight line, and is preferably larger in cross section than the primary restrictor channel 76, thus not significantly restricting the flow of medicament. Along the selector channel 78 are a plurality of nodes 82 that are each in fluid communication with a different portion of the primary restrictor channel 76. Each of the nodes 82 may be open or closed to allow or prevent fluid flow as will be described in greater detail later. As shown in FIG. 6, the selector knob 32 has a detent formed into its underside corresponding to each node 82. A varying number of closed nodes can be selected by rotating the selector knob 32 so the appropriate number of detents 84 are lined up with nodes 82, as illustrated in FIGS. 7A through 7F. A flexible membrane 86 is sandwiched between the top cover 12 and the selector knob 32. The membrane 86 is sufficiently thin and flexible to allow the detents 84 to push the membrane 86 into the nodes 82, closing off fluid flow through the node. The membrane 86 may consist of any suitable material, but a preferred material is polycarbonate having a thickness of about 2 to 3 mils.

Figure 8:
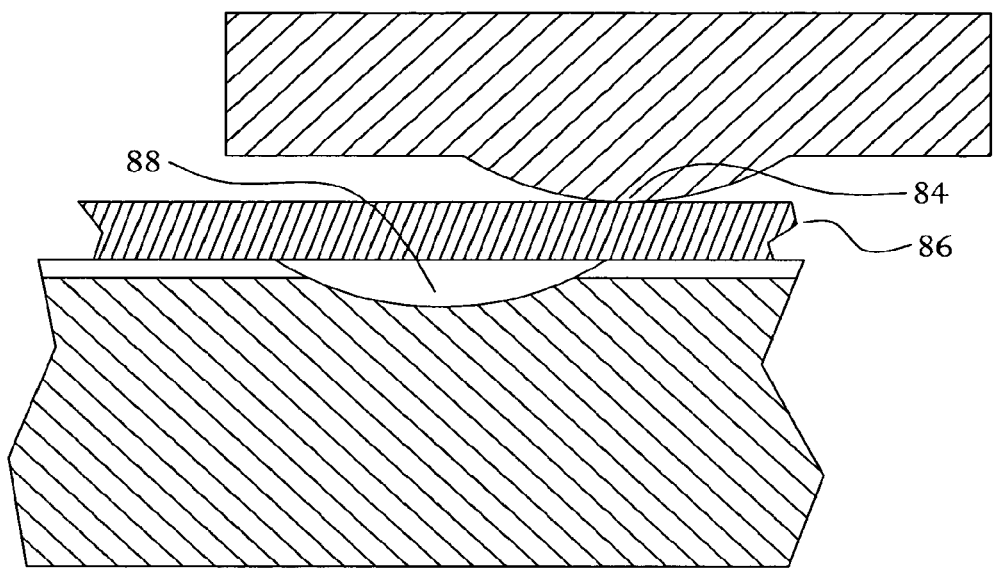
FIG. 8 is a cross-sectional view of a flow rate selection node in the open position.
Figure 9:
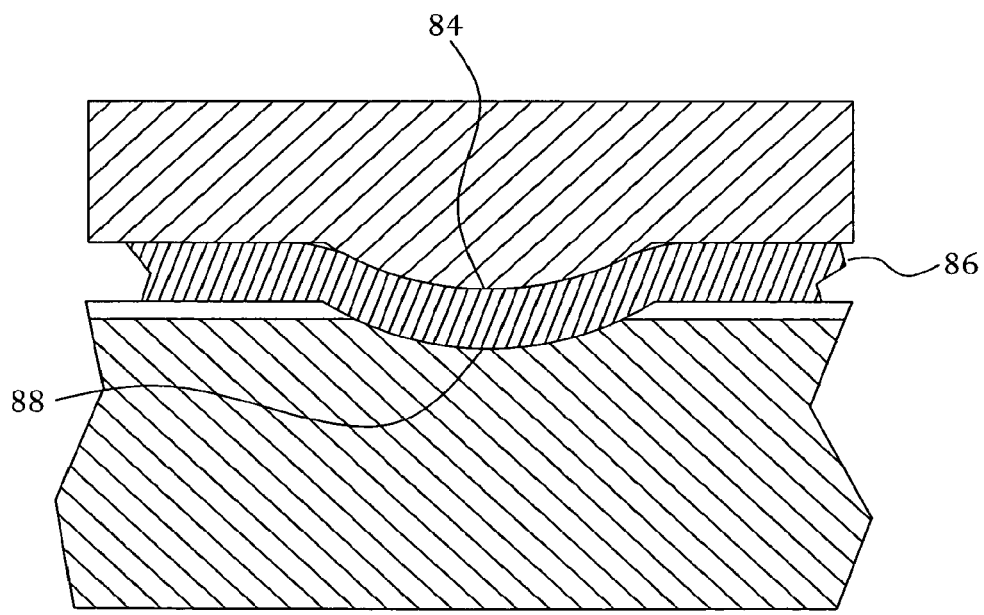
FIG. 9 is a cross-sectional view of a flow rate selection node in the closed position.

Each of the nodes 82 along the selector channel 78 work in conjunction with the selector knob 32 and the flexible membrane 86 to form a pinch valve, as shown in FIGS. 8 and 9. Each figure shows a cross section of a single node. Referring to FIG. 8, each of the nodes 82 are formed by an indentation 88 in the surface of the top cover 12 along the selector channel 78. The bottom of the selector knob 32 has detents 84 shaped to correspond to the node indentations 88. As shown in FIG. 8, when a detent 84 is not positioned directly over a node 82, the valve remains open, and fluid is free to pass through the node 82. As shown in FIG. 9, when a detent 84 is positioned over a node 82, the detent 84 pushes the flexible membrane 86 into the node 82, and closes the valve. Thus, fluid is not able to flow through the node.

Referring back to FIG. 6, when fluid flows from the reservoir 36 toward the cannula 48 and reaches the distal end of the initial channel 74, it can flow into either the primary restrictor channel 76 or the selector channel 78. If all of the nodes 82 are open, almost all of the fluid will flow through the selector channel 78 to the exit channel 80 because there is much less flow restriction. However, if the first node 90 is closed, fluid is forced to flow through the portion of primary restrictor channel 76 between the first 90 and second 92 node. Because the serpentine portion imparts more restriction on the flow than the selector channel 78, the total flow restriction is increased. If the remaining nodes 82 are left open, fluid will be able to avoid the remainder of the primary restrictor channel 76 by flowing into the selector channel 78 through the second node 92. By turning the selector knob 32 further, more nodes 82 are closed. Closing additional nodes forces the fluid through additional sections of the primary restrictor channel 76, increasing the flow restriction, and in turn lowering the flow rate. The maximum flow restriction (and minimum flow rate) is achieved when the selector knob 32 has been rotated so that all of the nodes 82 are closed and fluid is forced through the entire serpentine 76.

Figure 7A:
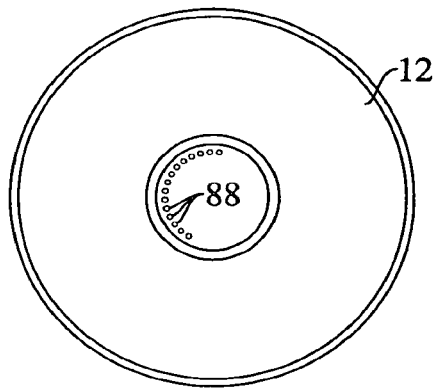
FIGS. 7A and 7B illustrate the operation of nodes in a first position.
Figure 7B:
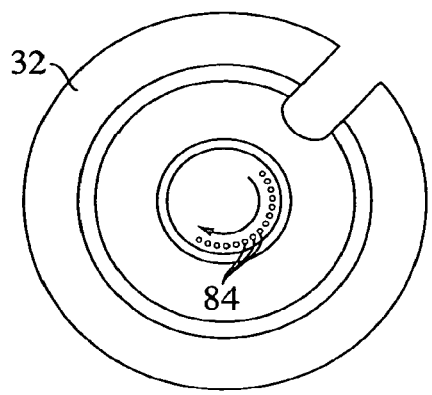
Figure 7C:
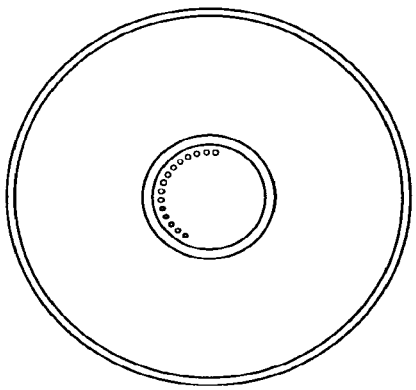
FIGS. 7C and 7D illustrate the operation of nodes in a second position.
Figure 7D:
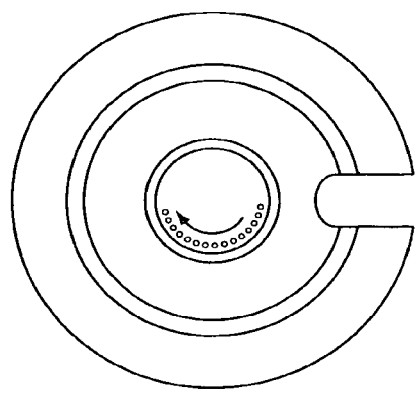
Figure 7E:
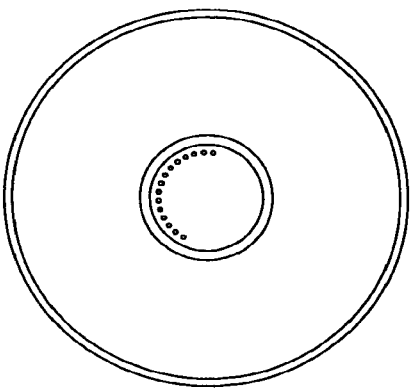
FIGS. 7E and 7F illustrate the operation of nodes in third position.
Figure 7F:
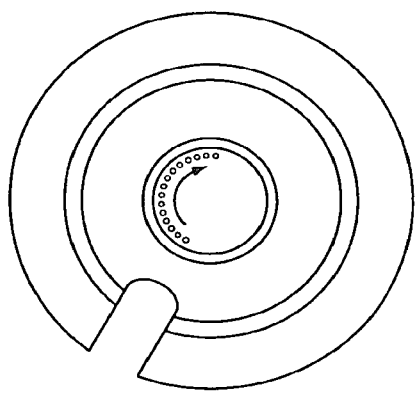

FIGS. 7A through 7F show schematically how the selector knob 32 can be turned to select different numbers of closed nodes. FIGS. 7A and 7B show the top cover 12 and selector knob 32 in a first position, such that none of the detents 84 are aligned with any of the node indentations 88. In this position all of the nodes are open and the flow rate is maximized. FIGS. 7C and 7D show the top cover 12 and selector knob 32 in a second position. As shown, five of the detents 84 line up with five of the node indentations 88. Thus, five nodes are closed, forcing fluid through the corresponding portions of primary restrictor channel 76. Finally, FIGS. 7E and 7F show the top cover 12 and selector knob 32 in a third position, such that all of the detents 84 line up with a node indentation 88. In this position, every node is closed, and fluid is forced through the entire primary restrictor channel 76, minimizing the flow rate.

The foregoing description describes the mechanism by which the device provides a basal flow rate of medicament to a patient. The following will describe how the device may also incorporate the ability to provide bolus injections. Bolus injections are particularly important with patients with diabetes, as they may need bolus injections of insulin with meals, for instance.

In one embodiment, the device 10 is provided with a bolus port. Once the device 10 has been activated, and the cannula has been inserted into the patient, the bolus port may be accessed to inject additional quantities of medicament, as needed, through the same cannula, thereby avoiding the inconvenience of additional needle sticks. Referring to FIGS. 1-3, the bolus port comprises an elastomeric septum 94 fixedly attached to the flexible membrane 86 over the central opening 44 in the top cover 12. The septum is held in place by a port guide 96. The port guide 96 is preferably a tall piece of plastic that is ultrasonically welded to the top cover 12, trapping the septum 94 in place. The port guide 96 also has a cone shaped interior that helps to guide a needle down to the septum 94. When a patient needs a bolus injection, they simply insert a syringe needle through the septum into the central opening 44 and inject. The additional dose is immediately carried into the body through the delivery cannula 48. When the injection has been completed, the syringe may be removed, and the septum 94 seals behind it, maintaining a hermetic seal within the device 10.

Figure 10:
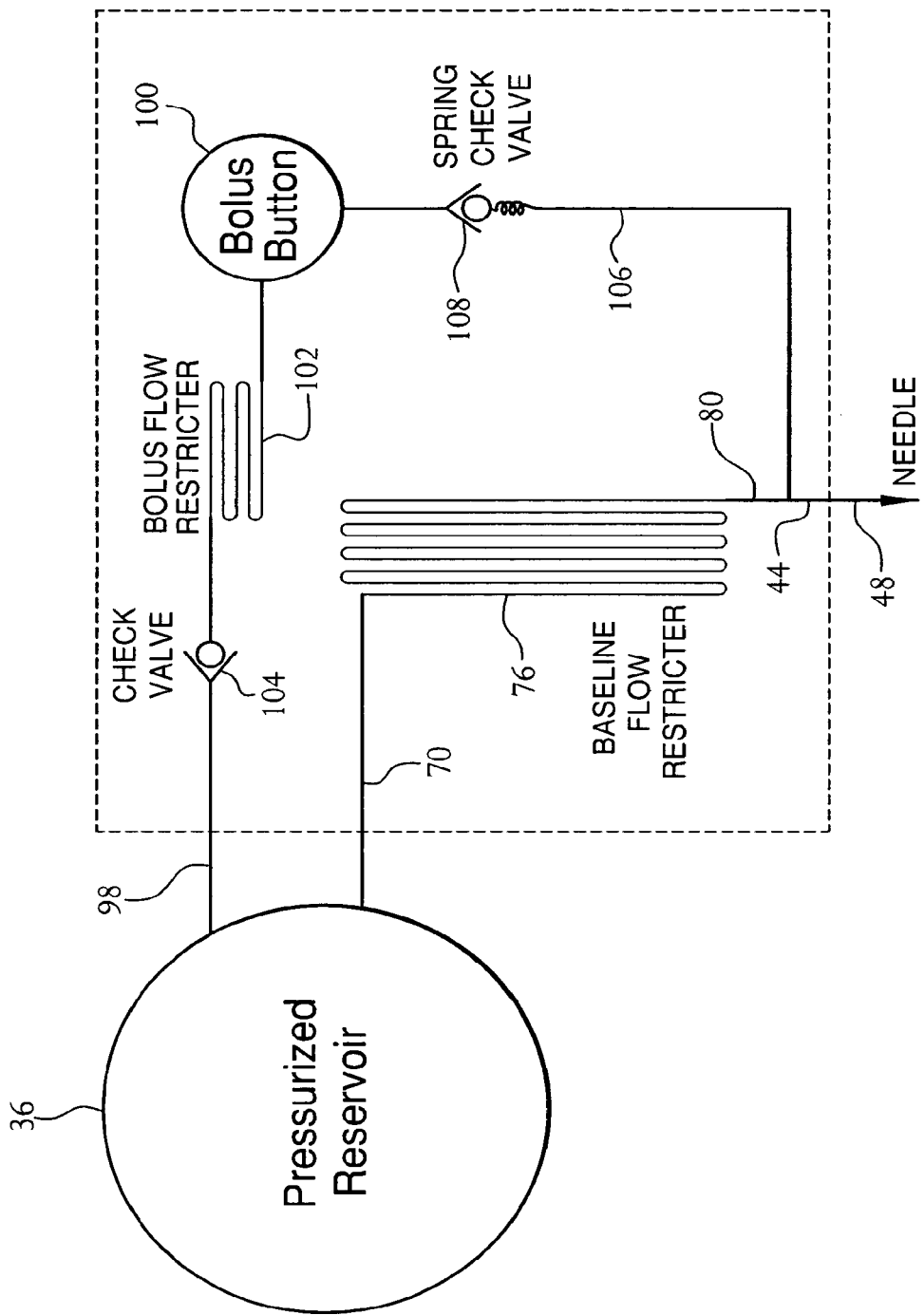
FIG. 10 is a schematic of a fluid delivery device according to the present invention including a flow rate limited bolus button.

In some applications, it may be important to limit the volume of medicament received through bolus injections. Once such application may be where the bolus injections are an opioid, although those skilled in the art will recognize that there are many such situations. The principles of the present invention may be applied to provide the device 10 with a bolus button. The bolus button allows the user to take bolus injections as needed, while limiting the amount of medicament delivered through the bolus button over a given time period. A schematic of a device 10 incorporating the bolus button is shown in FIG. 10.

A bolus restrictor channel 98 is incorporated into the surface of the top cover 12 as the previously discussed flow channels were. The bolus restrictor channel 98 has a proximal end and a distal end. The proximal end is in fluid communication with the reservoir 36, while the distal end is in fluid communication with a bolus button structure 100. The flexible membrane 68 forms one wall of the bolus flow channel 98. The bolus restrictor channel 98 preferably has a serpentine portion 102 to restrict the flow of medicament to the bolus button. The bolus restrictor channel 98 preferably incorporates a check valve 104 to prevent a reverse flow of medicament from the bolus button 100 back toward the reservoir 36. A bolus exit channel 106 has a proximal end in communication with the bolus button 100 and a distal end in communication with the exit channel 80 and the central opening 44. The bolus exit channel preferably incorporates a spring check valve 108 to prevent a backward flow of fluid from the exit channel 80 toward the bolus button 100. The spring check valve 108 also exerts spring pressure so that fluid cannot flow from the bolus button toward the central opening 44 without overcoming the spring pressure. This prevents medicament from flowing into the patient through the bolus flow channel 98 until the bolus button 100 is depressed.

The bolus button 100 is an indentation in the top cover 12 sealed with the flexible membrane 68. Fluid flows into and fills the space created between the bolus button indentation and the flexible membrane. Once the bolus button 100 is filled, the fluid remains in the bolus button 100 and cannot flow out due to check valve 104 and spring check valve 108.

In order to inject a bolus, the user presses down on the membrane 68 of the bolus button 100 causing the fluid within the bolus button 100 to become pressurized. Once the pressure in the bolus button 100 overcomes the spring pressure of the spring check valve 108, fluid exits the bolus button and flows out the bolus exit channel 106 toward the central opening 44 and the cannula 48. As the bolus button 100 empties, the flexible membrane 68 deforms into the bolus button indentation.

Once the bolus button 100 is empty, fluid will begin to flow into it from the reservoir 36. However, the rate at which the bolus button 100 refills is limited by the bolus restrictor channel 98. Thus, the maximum rate at which the user can take bolus injections is governed by the amount of restriction in the serpentine portion 102. Even if a patient continuously pushed the bolus button 100, they would only receive as much medicament with each push as would have flowed into the bolus button 100 since the previous push.

In another preferred embodiment, the cavity which defines the bolus button volume is provided with an adjustable plug. The plug is a threaded member that can be adjusted in or out of a threaded hole within the bolus button indentation in order to adjust the volume of the bolus button 100. Other means of altering the volume of the bolus cavity may be provided and are within the scope of the invention.

Figure 11:
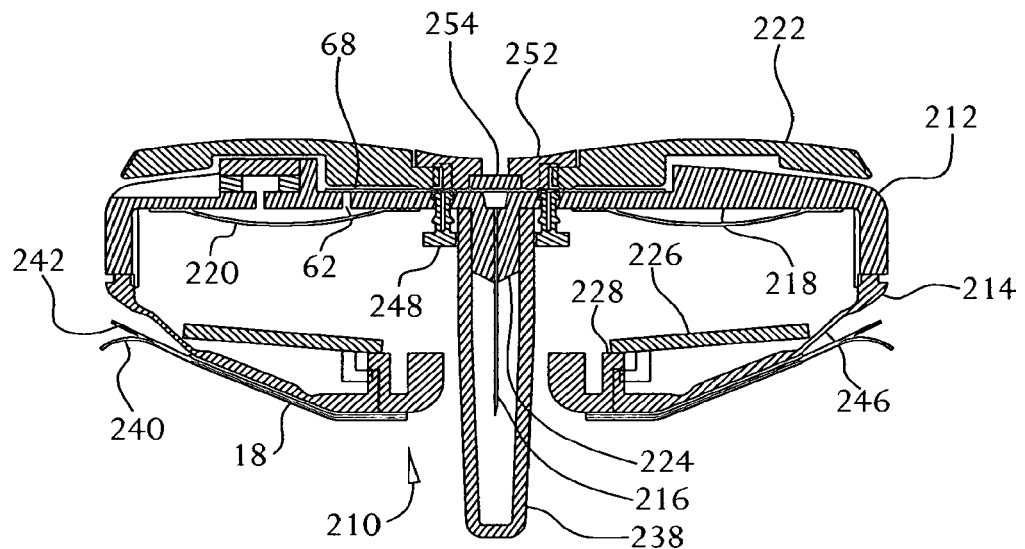
FIG. 11 is a cross-sectional view of a second embodiment of a fully assembled drug infusion device in the pre-use configuration.
Figure 12:
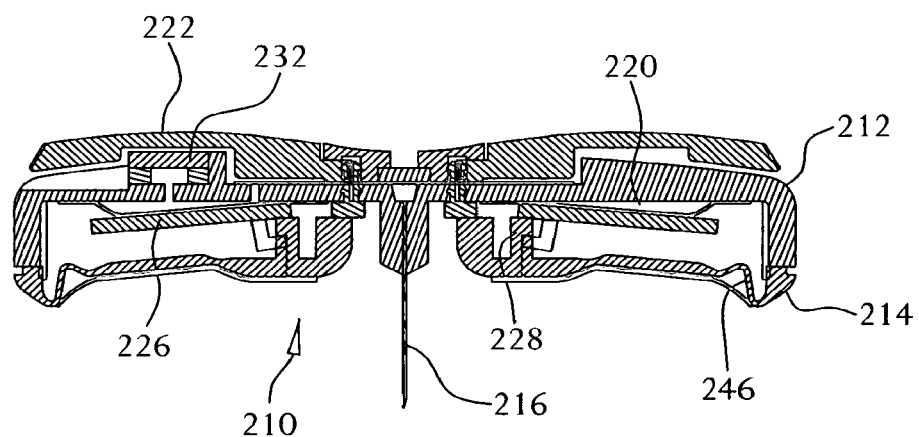
FIG. 12 is a cross-sectional view of a second embodiment of the drug infusion device shown in FIG. 11, in the active use configuration.
Figure 13:
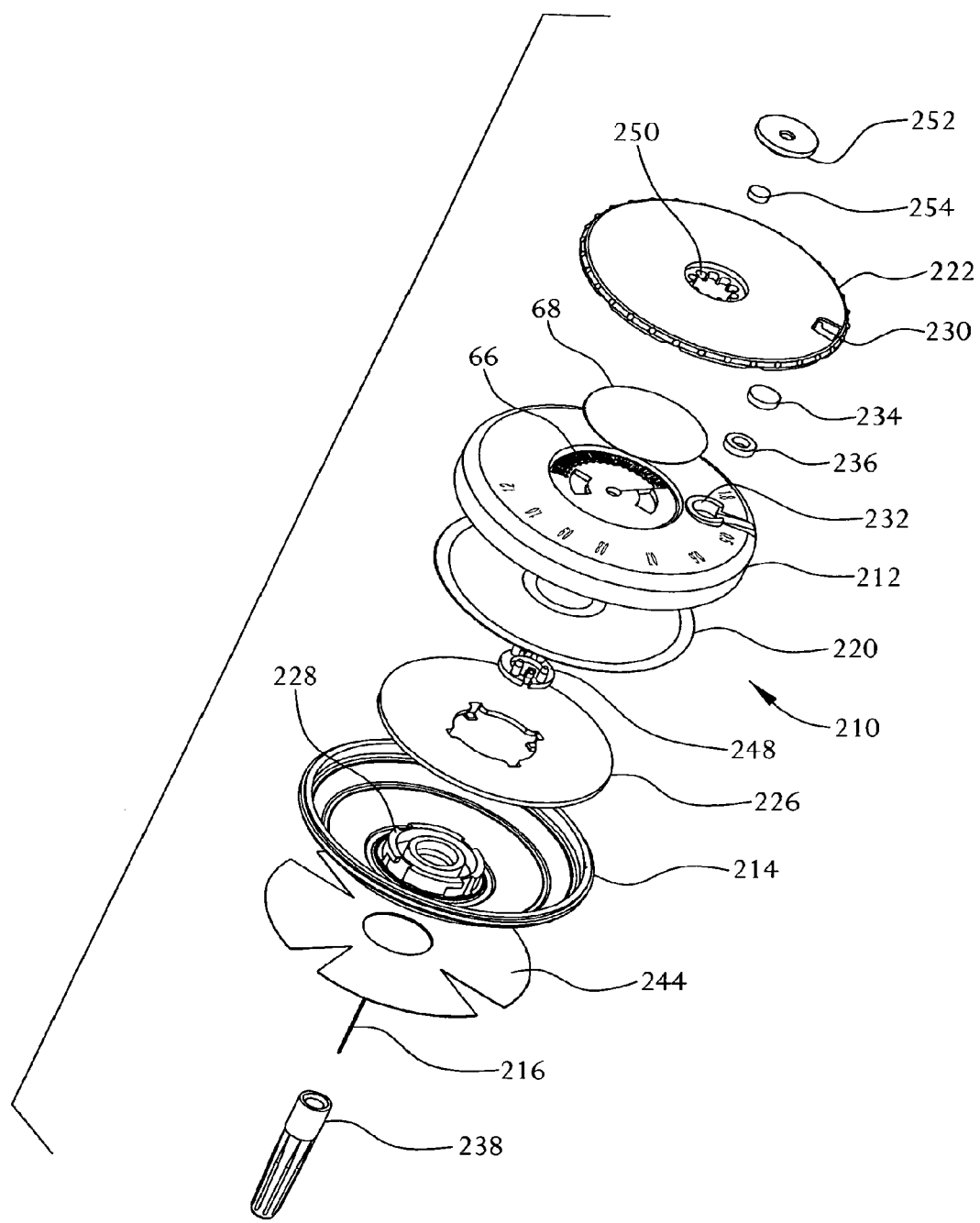
FIG. 13 is an exploded view of the infusion device shown in FIGS. 11 and 12.

FIGS. 11-13 illustrate a second embodiment 210 of the present invention. Referring to FIGS. 11-13 for the assembly of the second embodiment of the device, the two major components of the product are the top cover 212 and the collapsible bottom cover 214 which comes in contact with the skin of the user. The needle 216 for delivering the medicament is retained into the top cover 212 by an adhesive connection such as ultra-violet cured epoxy. Also on the inside surface 218 of the top cover the bladder membrane 220, in an annulus shape, is heat sealed to the surface 218 at both its inner diameter and outer diameter such that the medicament could be contained between it and the inside of the top cover 212. The assembly is held together by permanent connection of the bottom cover 214 to the top cover 212. A selector knob 222 is retained onto the top cover 212 by welded connection of the hub 252 to the top surface of the top cover 212 such that the selector knob 222 is free to rotate. Finally, a disc spring 226 is retained at its inner diameter to the bottom cover 214 onto a standing locator ring 228. The spring 226 is unstressed from the date of manufacture, and is not stressed until time of use of the product by the user.

As the product is shipped to the user (FIG. 11), the bottom cover 214 is domed outward so as to extend just beyond the height of the needle 216 hubbed into the top cover 212 as shown. To use the device, the user would first select the desired flow rate using the selector knob 222 on the top of the unit. As the selector knob 222 is rotated, it will give an audible and tactile click as it passes through each flow rate, and the rate at any given position can be read through the port 230 on the selector knob (see FIG. 13). Once the rate is selected, the user would then fill the unit using a simple filling device with a sharp needle with the proper amount of medicament through the fill port 232 which is comprised of (see FIG. 12) an elastomeric fill port septum 234 which is secured to the top cover 212 at the port location 232 by means of a septum cap 236. Since the unit is intended to be worn for a 24 hour period, regardless of flow rate, a different volume of medicament would need to be inserted into the unit for each flow rate selected. Therefore, a feature of the present invention would comprise a physical stop for the filling device plunger which is at a different depth for each flow rate selected using the selector knob 222 in the previous step. Referring again to FIG. 11, after filling the unit, the user would remove the shield 238, exposing the still hidden needle 216 under the unit. Then the user would peel off the release liner 240 from the adhesive carrier 242 on the bottom cover 214 (note that the adhesive carrier 242 is only adhered to the bottom cover 214 in the area shown by the adhesive layer 244 while the carrier 242 is adhered to the skin of the user over its entire area.) The unit would then be adhered to the skin of the patient at a suitable location such as on the abdomen.

To activate the unit, the user would then press firmly down on the unit so as to cause the thin outer perimeter 246 of the bottom cover 214 to collapse inward and allow the bottom cover 214 to fold into the recess in the top cover 212. As the bottom cover 214 collapses into the top cover 212 the needle 216, which is attached to the top cover 212, will by virtue of this attachment, travel downward through the opening in the bottom cover 214 and into the skin of the user. Note in FIG. 12 how the needle 216 protrudes beyond the bottom surface of the bottom cover 214. Then, as the bottom cover 214 collapses into the top cover 212 the spring 226 is forced into contact with the bladder 220 containing the medicament. This spring force causes the disc spring 226 to deflect downward into its zero spring-rate range and therefore imparts a precise pressure upon the medicament in the bladder 220 which would initiate the flow of the medicament into the skin. Finally, as the bottom cover 214 collapses inward the inner ring of the bottom cover 214 contacts the locking ring 248 and forces it upward through holes in the top cover 212 and into the teeth 250 of the inner diameter of the selector knob 222. This locks the selector knob 222 into place such that the flow rate cannot be either inadvertently or intentionally moved to another setting after initiation of flow.

To remove the product, the user simply pull upward on the unit, away from the skin, until the collapsed bottom cover 214 pops back out to its domed position as in FIG. 11 and the unit will then be in a safe position, and the needle will be retracted from the skin. At this point the user can simply peel the device from the skin, replace the shield 238 over the needle 216 if desired, and discard. It should also be noted that after activation of the unit, the selector knob cannot be rotated, even after retracting the needle. If the lock ring 248 forces the selector knob 222 to rotate slightly upon activation then the fill port 232 will be occluded such that the unit cannot then be refilled thereby forcing the product to be single-use.

Finally, referring to FIGS. 11-13, the second embodiment also includes a bolus port on the top of the unit to enable the user to immediately inject a measured quantity of medicament directly into the skin through the unit's needle 216. This allows the user to take a quick dose of medication without having to resort to an additional needle stick. The bolus port is incorporated into the hub 252 retaining the selector knob 222 to the top of the top cover 212. The port is ultrasonically welded to the top surface of the top cover 212 thereby trapping the elastomeric septum 254 between the membrane seal 68 and the bolus port. In this manner, the septum 254 acts as a self-sealing needle port, connecting directly to the node immediately upstream of the needle 216. The bolus port can be used at any time during which the unit is adhered to the body and the needle is set into the skin.

Although the present invention has been described in reference to certain preferred embodiments thereof, it will be understood that the invention is not limited to the details of these embodiments. Various substitutions and modifications have been described in the course of the foregoing description, and other substitutions and modifications will occur to those of ordinary skill in the art. All such substitutions and modifications are intended to fall within the scope of the invention as defined in the appended claims.

What is claimed is:

1. A device for delivering fluid at a constant selectable flow rate comprising: a housing; a reservoir in said housing for containing a supply of said fluid and for delivering said fluid under pressure; an adjustable flow channel having a proximal end and a distal end and a selectable flow distance therebetween, said proximal end being in fluid communication with said reservoir; and a delivery cannula in fluid communication with said distal end of said flow channel for delivering said fluid; wherein said selectable flow distance is determined by opening and closing a plurality of valves, the plurality of valves comprising a plurality of detents rotatably alignable with a plurality of indentations with a flexible membrane therebetween, each valve being in fluid communication with a corresponding flow section of said flow channel, and each corresponding flow section of said flow channel is a portion of said selectable flow distance, thereby providing an adjustable flow rate through said flow channel by variation of said selectable flow distance of said flow channel.

2. A device as claimed in claim 1 wherein a portion of said flow channel is formed into said housing.

3. A device as claimed in claim 2 wherein at least one wall of said flow channel is formed by the flexible membrane.

4. A device as claimed in claim 3 wherein said valves are defined by indentations in said housing, said device further having a flow rate selection device movably connected to said housing, said flexible membrane disposed between said housing and said flow rate selection device, said flow rate selection device further having a plurality of detents adapted to match said indentations such that said detents may be moved into alignment with any number of said indentations causing the corresponding valves to be closed.

5. A device as claimed in claim 1, wherein said reservoir comprises at least one spring element for pressurizing said fluid contained in said reservoir.

6. A device as claimed in claim 5, wherein said spring element is a disc spring.

7. A device as claimed in claim 1 further having a resealable port in fluid communication with said delivery cannula for immediate delivery of additional fluid.

8. A device as claimed in claim 7, wherein said flow channel further comprises a check valve adapted to prevent the flow of fluid toward said reservoir.

9. A device as claimed in claim 1, wherein a first flow section has a greater cross sectional area than a second flow section.

10. A device as claimed in claim 1 wherein said flow channel is formed in a serpentine pattern.

11. The device as claimed in claim 1 further comprising a self-sealing needle port in fluid communication with said delivery cannula.

12. A device as claimed in claim 1, wherein said flow channel further comprises a check valve adapted to prevent the flow of fluid toward said reservoir.

* * * * *